US012788944B2

(12) United States Patent
Shreve

(10) Patent No.: US 12,788,944 B2
(45) Date of Patent: Nov. 10, 2026

(54) CATHETER DEVICES INCLUDING EXPANDABLE FLUID DELIVERY ELEMENTS AND METHODS FOR USING SAME

(71) Applicant: BARD PERIPHERAL VASCULAR, INC., Franklin Lakes, NJ (US)

(72) Inventor: Samuel Michael Shreve, Scottsdale, AZ (US)

(73) Assignee: BARD PERIPHERAL VASCULAR, INC., Franklin Lakes, NJ (US)

( * ) Notice: Subject to any disclaimer, the term of this patent is extended or adjusted under 35 U.S.C. 154(b) by 413 days.

(21) Appl. No.: 18/561,149

(22) PCT Filed: Oct. 12, 2022

(86) PCT No.: PCT/US2022/077953
§ 371 (c)(1),
(2) Date: Nov. 15, 2023

(87) PCT Pub. No.: WO2024/081019
PCT Pub. Date: Apr. 18, 2024

(65) Prior Publication Data

US 2025/0073426 A1 Mar. 6, 2025

(51) Int. Cl.
*A61M 25/00* (2006.01)

(52) U.S. Cl.
CPC . *A61M 25/0084* (2013.01); *A61M 2025/0087* (2013.01)

(58) Field of Classification Search
CPC .... A61M 2025/105; A61M 2025/0057; A61M 2025/1086; A61M 25/0074; A61M 2025/0087
See application file for complete search history.

(56) References Cited

U.S. PATENT DOCUMENTS 5,279,565 A * 1/1994 Klein .................. A61M 25/007 606/198
5,419,777 A * 5/1995 Hofling ............. A61M 25/0069 128/831
5,681,281 A * 10/1997 Vigil ..................... A61M 25/10 604/103.01
5,693,029 A * 12/1997 Leonhardt ............ A61M 29/02 604/523
6,280,413 B1 * 8/2001 Clark ...................... A61F 2/013 604/103.08

(Continued)

FOREIGN PATENT DOCUMENTS

WO WO-9306885 A1 * 4/1993 ............ A61M 25/04

*Primary Examiner* — William R Carpenter
(74) *Attorney, Agent, or Firm* — Dinsmore & Shohl LLP

(57) ABSTRACT

Methods and use for a catheter device configured to deliver a plurality of therapeutic fluids simultaneously, in which the catheter device includes a hub, a guidewire tube extending from the hub, a plurality of fluid delivery elements extending from the hub and disposed about the guidewire tube, and a compression sheath disposable over and slidably movable relative to the plurality of fluid delivery elements. The elements are naturally biased when the compression sheath does not cover the hinge portion of each of the plurality of fluid delivery elements, and are in compressed when the compression sheath covers the hinge portion of each of the elements.

18 Claims, 11 Drawing Sheets

(56) References Cited

U.S. PATENT DOCUMENTS

| | | | | |
|---|---|---|---|---|
| 6,283,947 | B1 * | 9/2001 | Mirzaee ................ | A61M 25/10 604/264 |
| 6,302,870 | B1 * | 10/2001 | Jacobsen ................ | A61B 17/22 604/170.03 |
| 6,547,767 | B1 * | 4/2003 | Moein ............... | A61M 25/0084 606/145 |
| 7,837,670 | B2 * | 11/2010 | Barath ............... | A61M 25/1011 604/517 |
| 8,007,470 | B2 * | 8/2011 | Shirley ............. | A61M 25/0084 604/164.01 |
| 9,278,196 | B2 * | 3/2016 | Fischell ............ | A61M 25/0084 |
| 2005/0033236 | A1 * | 2/2005 | Wijay ............... | A61M 25/0084 604/164.01 |
| 2007/0250035 | A1 * | 10/2007 | El-Nounou ....... | A61M 25/0082 604/509 |
| 2011/0295228 | A1 | 12/2011 | Shirley | |
| 2019/0201070 | A1 | 7/2019 | Fischell | |
| 2021/0220615 | A1 | 7/2021 | Orth | |

* cited by examiner

CATHETER DEVICES INCLUDING EXPANDABLE FLUID DELIVERY ELEMENTS AND METHODS FOR USING SAME

This application is a U.S. national phase of International Application No. PCT/US22/77953, filed Oct. 12, 2023, which is incorporated herein by reference in its entirety.

TECHNICAL FIELD

The present specification generally relates to catheter devices for delivering a therapeutic fluid and, more specifically, catheter devices with expandable fluid delivery elements configured to puncture a vessel wall when delivering a therapeutic fluid.

BACKGROUND

Therapeutic fluids may be introduced into a vessel to achieve a biological effect such as, for example, inducing hemostasis, reducing likelihood of restenosis, or treating cancerous tumors or other diseases. Therapeutic agents may be injected using an intravenous technique and it may be desirable to provide localized or targeted delivery of the therapeutic fluid, which may allow for the precise delivery of agents at specific target sites.

Catheter devices may be configured to locally deliver a single therapeutic fluid to a vessel at a given time. Such singular delivery may result in limited treatment to a particular area at any one time. To deliver therapeutic fluids as multiple fluids and/or to different areas, multiple catheter devices may need to be provided or the catheter device being used may need to need to be decoupled to the existing fluid supply and coupled to a different fluid supply for each delivery, which may require additional time and increase the risk of damage to the catheter device and/or to the subject.

Accordingly, a need exists for improved catheter devices to deliver one or more therapeutic fluids to different portions of a vessel simultaneously.

SUMMARY

In one embodiment, a catheter device comprises: a hub including a plurality of ports, each port of the plurality of ports configured to receive a fluid; a guidewire tube extending from the hub and defining a guidewire lumen including a longitudinal axis; a plurality of fluid delivery elements extending from the hub and disposed about the guidewire tube, each fluid delivery element of the plurality of fluid delivery elements including a proximal portion, a distal portion, a hinge portion therebetween, and one or more needles on the distal portion extending in a direction perpendicular to the longitudinal axis of the guidewire lumen, a distal end of each fluid delivery element configured to adjust between (i) a naturally biased and expanded position at a spaced distance from the guidewire tube in which the proximal portion is angled with respect to the distal portion via the hinge portion and (ii) a compressed and retracted position abutting the guidewire tube in which the proximal portion is in alignment with the distal portion; and a compression sheath disposable over and slidably movable relative to the plurality of fluid delivery elements, wherein the plurality of fluid delivery elements are naturally biased in the naturally biased and expanded position when the compression sheath is proximally disposed in an expansion permitting position in which the compression sheath does not cover the hinge portion of each of the plurality of fluid delivery elements, and wherein the plurality of fluid delivery elements are in the compressed and retracted position when the compression sheath is distally disposed in a covering position in which the compression sheath covers the hinge portion of each of the plurality of fluid delivery elements.

In another embodiment, a catheter device comprises: a hub including a plurality of ports, each port of the plurality of ports configured to receive a fluid; a guidewire tube extending from the hub and defining a guidewire lumen including a longitudinal axis; a plurality of fluid delivery elements extending from the hub and disposed about the guidewire tube, each fluid delivery element of the plurality of fluid delivery elements including a proximal portion, a distal portion, a hinge portion therebetween, and one or more needles on the distal portion extending in a direction perpendicular to the longitudinal axis of the guidewire lumen, a distal end of each fluid delivery element configured to adjust between (i) a naturally biased and expanded position at a spaced distance from the guidewire tube in which the proximal portion is angled with respect to the distal portion via the hinge portion and (ii) a compressed and retracted position abutting the guidewire tube in which the proximal portion is in alignment with the distal portion; and a compression sheath disposable over and slidably movable relative to the plurality of fluid delivery elements, wherein the plurality of fluid delivery elements are naturally biased in the naturally biased and expanded position when the compression sheath is proximally disposed in an expansion permitting position in which the compression sheath does not cover the hinge portion of each of the plurality of fluid delivery elements, and wherein the plurality of fluid delivery elements are in the compressed and retracted position when the compression sheath is distally disposed in a covering position in which the compression sheath covers the hinge portion of each of the plurality of fluid delivery elements, wherein each needle of the one or more needles on a respective fluid delivery element includes a needle lumen that is in fluid communication with a corresponding port of the plurality of ports of the hub through a corresponding fluid delivery lumen of the respective fluid delivery element of the plurality of fluid delivery elements, and each needle of the one or more needles includes a taper at a distal end of the needle.

In yet another embodiment, a method of delivering a therapeutic fluid to a vessel comprises: positioning a catheter device within the vessel, the catheter device including: a hub including a plurality of ports, each port of the plurality of ports configured to receive a fluid; a guidewire tube extending from the hub and defining a guidewire lumen including a longitudinal axis; a plurality of fluid delivery elements extending from the hub and disposed about the guidewire tube, each fluid delivery element of the plurality of fluid delivery elements including a proximal portion, a distal portion, a hinge portion therebetween; and one or more needles on the distal portion extending in a direction perpendicular to the longitudinal axis of the guidewire lumen, a distal end of each fluid delivery element configured to adjust between (i) a naturally biased and expanded position at a spaced distance from the guidewire tube in which the proximal portion is angled with respect to the distal portion via the hinge portion and (ii) a compressed and retracted position abutting the guidewire tube in which the proximal portion is in alignment with the distal portion, and a compression cover sheath disposable over and slidably movable relative to the plurality of fluid delivery elements; and moving the compression sheath of the catheter device proximally toward the hub to move from (i) a covering position in which the compression sheath covers the hinge portion of each of the plurality of fluid delivery elements such that the plurality of fluid delivery elements are in the compressed and retracted position to (ii) an expansion permitting position in which the needle cover sheath does not cover the hinge portion of each of the plurality of fluid delivery elements such that the plurality of fluid delivery elements are in the naturally biased and expanded position.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
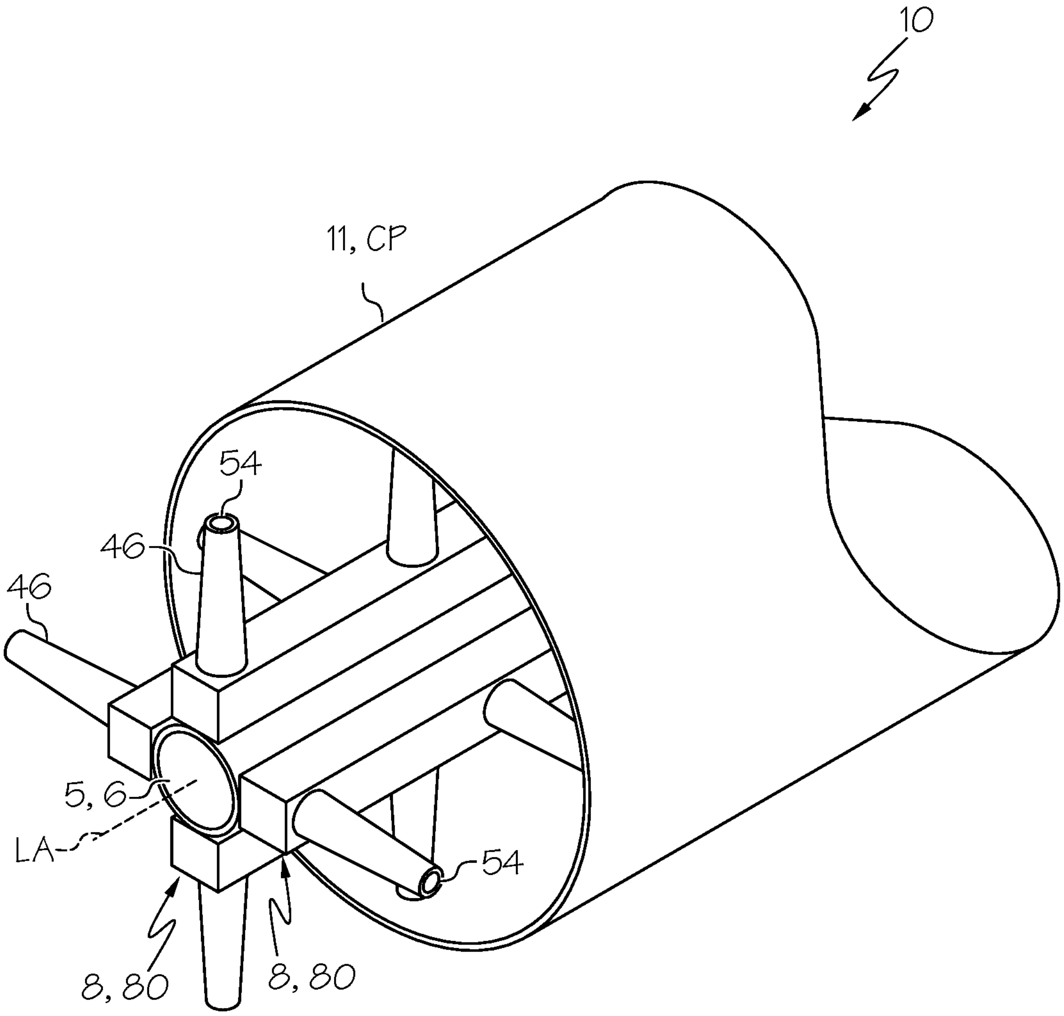
FIG. 1 schematically depicts a partial perspective view of a catheter device with a plurality of fluid delivery elements in a compressed and retracted position within a compression sheath, according to one or more embodiments shown and described herein.

Embodiments described herein are directed to a catheter device 10 of FIGS. 1-4 or a catheter device 100 of FIGS. 5-12 configured to deliver a plurality of therapeutic fluids simultaneously. As described in greater detail further below, the catheter device 10, 100 may include a hub 4, 104, a proximal hub 102 (FIGS. 5-12) distally connected to the hub 104, a guidewire tube 5, 105 extending from the hub 4, 104 and defining a guidewire lumen 6, 106, a plurality of fluid delivery elements 8, 108 extending from the hub 4, 104, a compression sheath 11, 111 disposable over and slidably movable relative to the plurality of fluid delivery elements 8, 108. In embodiments, as shown in FIGS. 5-12, the catheter device 100 may further include a needle cover sheath 112 (FIGS. 5-12) disposed over the compression sheath 111 and movable relative to the compression sheath 111, the guidewire lumen 106, and the plurality of fluid delivery elements 108. The fluid delivery elements 8, 108 of the catheter device 10, 100 may be configured to adjust between a naturally biased and expanded position 90, 190 (FIGS. 4, 6) at a spaced distance from the guidewire tube 5, 105, and a compressed and retracted position 80, 180 (FIGS. 1, 5) abutting the guidewire tube 5, 105. Various embodiments of the catheter device and the operation of the catheter device are described in more detail herein. Whenever possible, the same reference numerals will be used throughout the drawings to refer to the same or like parts.

In non-limiting embodiments, a catheter device 10, 100 (shown respectively in FIGS. 1-4 and FIGS. 5-12) may include a hub 4, 104 including a plurality of ports 19, 119. Each port 19, 119 is configured to receive a fluid. The catheter device 10, 100 further includes a guidewire tube 5, 105 extending from the hub 4 and defining a guidewire lumen 6, 106. The guidewire lumen 6, 106 includes a longitudinal axis LA. The catheter device 10, 100 further includes a plurality of fluid delivery elements 8, 108 extending from the hub 4, 104 and disposed about the guidewire tube 5, 105. Each fluid delivery element 8, 108 includes a proximal portion 40, 140, a distal portion 42, 142, a hinge portion 44, 144 therebetween, and one or more needles 46, 146 on the distal portion 42, 142 extending at least in a direction perpendicular to the longitudinal axis LA of the guidewire lumen 6, 106. It will be understood that in some embodiments, one or more of the needles 46, 146 may also extend partially in a direction parallel to the longitudinal axis LA of the guidewire lumen 6, 106, so long as in use the needles 46, 146 are configured to penetrate a vessel wall. Each needle 46, 146 on a respective fluid delivery element 8, 108 comprises a needle lumen 54, 154 that is in fluid communication with a corresponding port 19, 119 of the hub 4 through a corresponding fluid delivery lumen 121 (not shown in FIGS. 1-4; shown in FIG. 10) of the respective fluid delivery element 8, 108, and each needle 46, 146 may include a taper at a distal end of the needle 46, 146. The distal end of the needle 46, 146 may be spaced away and extending in a direction facing away from the guidewire tube 5, 105.

A distal end of each fluid delivery element 8, 108 is configured to adjust between (i) a naturally biased and expanded position 90, 190 (FIGS. 4, 6) at a spaced distance from the guidewire tube 5, 105 in which the proximal portion 40, 140 is angled with respect to the distal portion 42, 142 via the hinge portion 44, 144, and (ii) a compressed and retracted position 80, 180 (FIGS. 1, 5) abutting the guidewire tube 5, 105 in which the proximal portion 40, 140 is in alignment with the distal portion 42, 142. The catheter device 10, 100 further includes a compression sheath 11, 111 disposable over and slidably movable relative to the plurality of fluid delivery elements 8, 108.

The plurality of fluid delivery elements 8, 108 are naturally biased in the naturally biased and expanded position 90, 190 (FIGS. 4, 6) when the compression sheath 11, 111 is proximally disposed in an expansion permitting position EPP in which the compression sheath 11, 111 does not cover the hinge portion 44, 144 of each of the plurality of fluid delivery elements 8, 108. The plurality of fluid delivery elements 8, 108 are in the compressed and retracted position 80, 180 (FIGS. 1, 5) when the compression sheath 11, 111 is distally disposed in a covering position CP in which the compression sheath 11, 111 covers the hinge portion 44, 144 of each of the plurality of fluid delivery elements 8, 108.

In embodiments, the plurality of fluid delivery elements 8, 108 may include at least two fluid delivery elements 8, 108 spaced apart on a shared plane that each element 8, 108 intersects. Additionally or alternatively, the plurality of fluid delivery elements 8, 108 may include at least four fluid delivery elements 8, 108, each of the plurality of fluid delivery elements 8, 108 equidistantly spaced apart from one another. Other combinations and spacing of the plurality of fluid delivery elements 8, 108 are within the scope of and contemplated by this disclosure.

Referring now to the catheter 10 of FIGS. 1-4, FIG. 1 illustrates the catheter device 10 with the plurality of fluid delivery elements 8 in the compressed and retracted position 80 within the compression sheath 11. It is contemplated within this disclosure that the catheter devices 10, 100 may be used for delivering a therapeutic fluid to a vessel via a method including positioning the catheter device 10 within the vessel. As shown in FIG. 1 and described herein, the catheter device 10 includes the guidewire tube 5 defining the guidewire lumen 6 that comprises a longitudinal axis LA. The plurality of fluid delivery elements are disposed about the guidewire tube 5. The one or more needles 46, including needle lumens 54, extend in a direction perpendicular to the longitudinal axis LA of the guidewire lumen 6.

The compression sheath 11 is disposable over and slidably movable relative to the plurality of fluid delivery elements 8. The catheter device 10 of FIG. 1 is shown in a covering position CP in which the compression sheath 11 covers the hinge portion 44 (FIGS. 2-4) of each of the plurality of fluid delivery elements 8 such that the plurality of fluid delivery elements 8 are in the compressed and retracted position 80 (shown in FIGS. 1-3).

Figure 2:
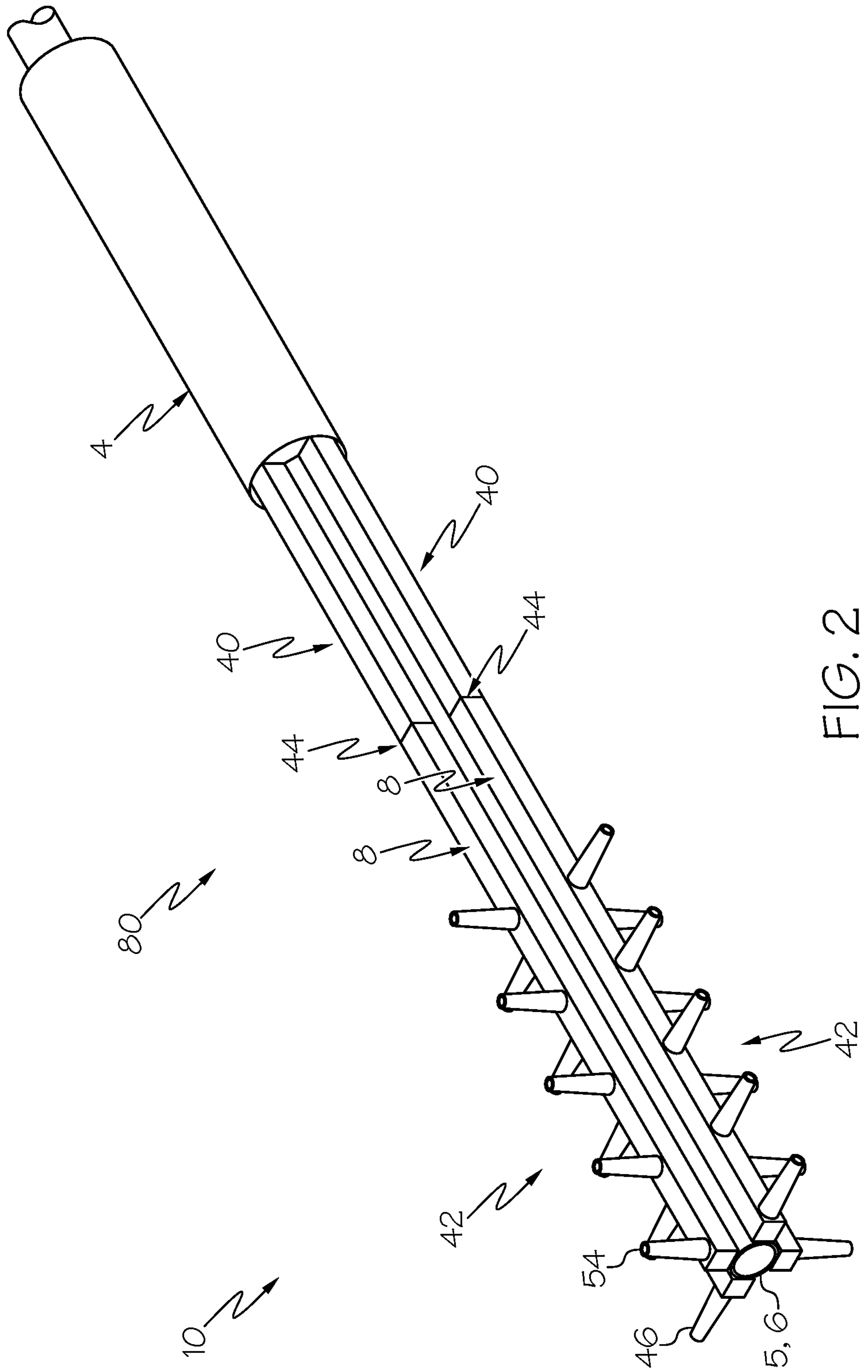
FIG. 2 schematically depicts a perspective distal view of the catheter device of FIG. 1 with the plurality of fluid delivery elements in the compressed and retracted position and with the compression sheath omitted for visibility, according to one or more embodiments shown and described herein.
Figure 3:
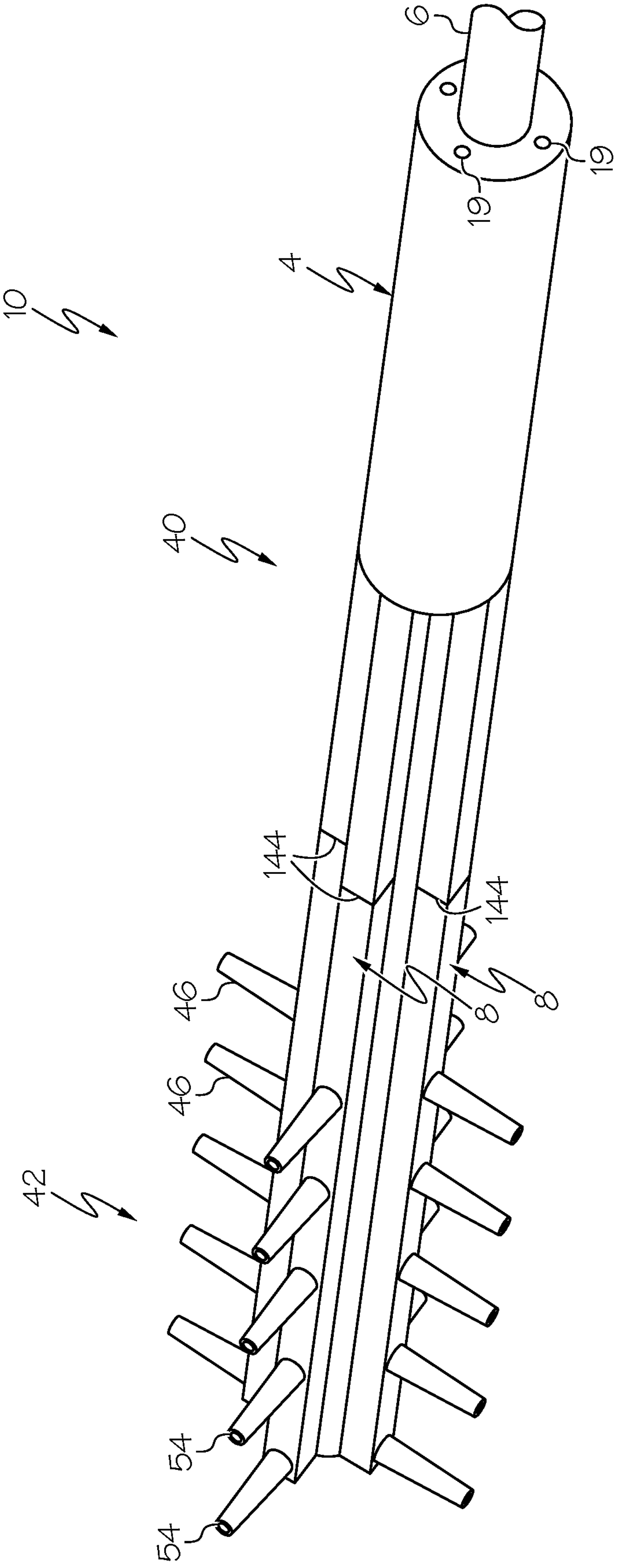
FIG. 3 schematically depicts a perspective proximal view of the catheter device of FIG. 1 with the plurality of fluid delivery elements in the compressed and retracted position and with the compression sheath omitted for visibility.

FIG. 2 illustrates a distal perspective view of the catheter device 10 with the plurality of fluid delivery elements 8 in the compressed and retracted position 80 and with the compression sheath 11 omitted for visibility. FIG. 3 illustrates a proximal perspective view of the catheter device 10 with the plurality of fluid delivery elements 8 in the compressed and retracted position 80 and with the compression sheath 11 omitted for visibility.

As shown in FIGS. 2-3, the catheter device 10 includes a hub 4 including a plurality of ports 19 (FIG. 3) configured to receive a fluid. The guidewire tube 5 and the plurality of fluid delivery elements 8 extend from the hub 4. Each fluid delivery element 8 respectively includes a proximal portion 40, a distal portion 42, a hinge portion 44 therebetween. The one or more needles 46 on the distal portion 42 of each fluid delivery element 8 extends in a direction perpendicular to the longitudinal axis LA of the guidewire lumen. A distal end of each fluid delivery element 8 is configured to adjust between (i) the naturally biased and expanded position 90 (FIG. 4) at a spaced distance from the guidewire tube 5 in which the proximal portion 40 of each fluid delivery element 8 is angled with respect to the distal portion 42 via the hinge portion 44 and (ii) a compressed and retracted position 80 (FIGS. 1-3), the distal end of each fluid delivery element 8 abutting the guidewire tube 5 and in which the proximal portion 40 of each fluid delivery element 8 is in alignment with the distal portion 42 of the respective fluid delivery element 8.

As shown in FIG. 3, each needle 46 includes a needle lumen 54 that is in fluid communication with a corresponding port 19 of the plurality of ports 19 of the hub 4 through a corresponding lumen of the respective fluid delivery element 8 of the plurality of fluid delivery elements. The therapeutic fluid may be delivered from the hub 4 through the plurality of ports 19 of the hub 4 through a corresponding fluid delivery lumen of each of the plurality of fluid delivery elements 8 and through a corresponding needle lumen 54 of each needle 46.

Figure 4:
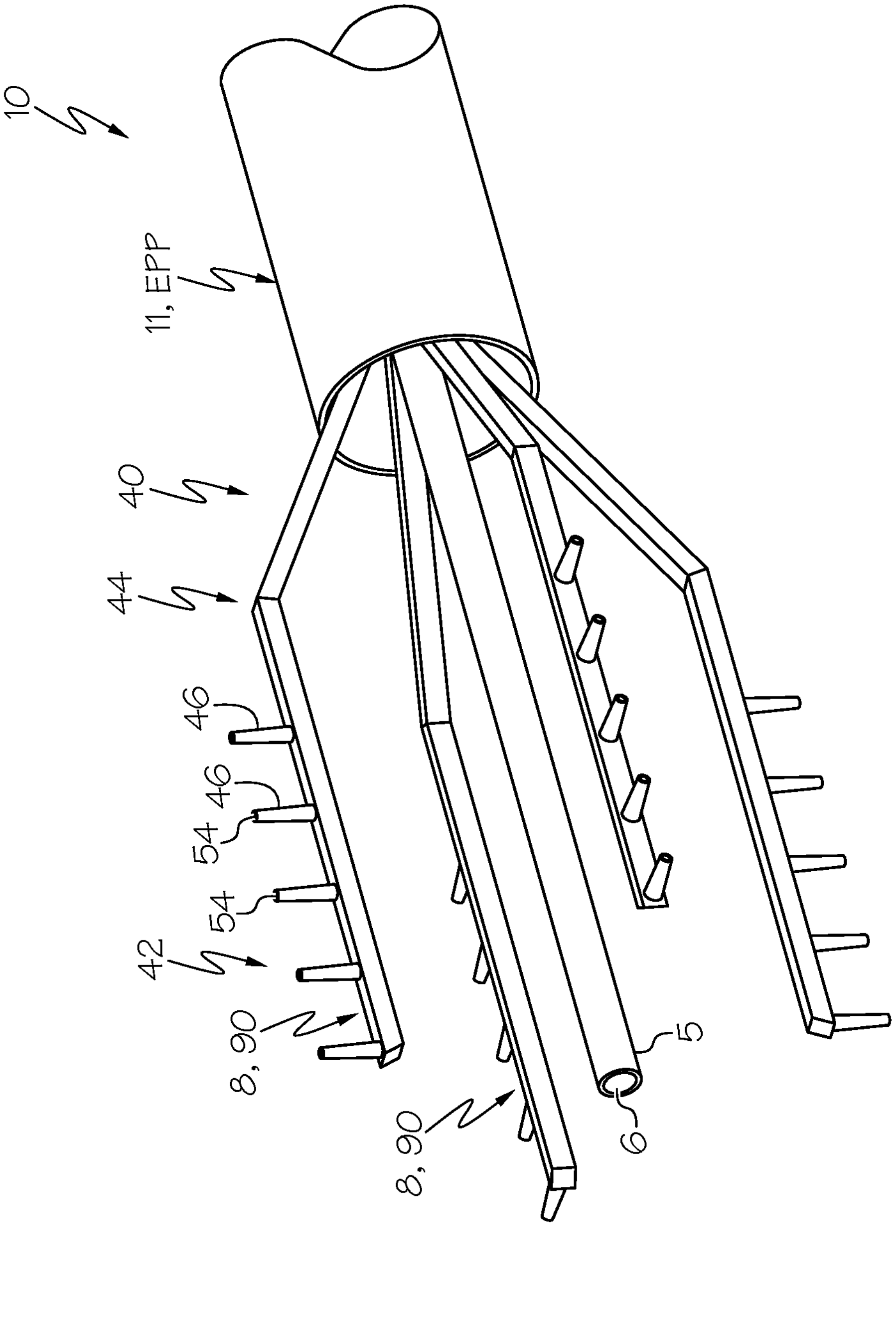
FIG. 4 schematically depicts a perspective view of the catheter device of FIG. 1 in with the plurality of fluid delivery elements in a naturally biased and expanded position extending from the compression sheath.

FIG. 4 illustrates the catheter device 10 with the plurality of fluid delivery elements 8 in a naturally biased and expanded position 90 extending from the compression sheath 11. The compression sheath 11 of the catheter device 10 may be moved proximally toward the hub 4 to move from (i) the covering position CP of FIG. 1 in which the compression sheath 11 covers the hinge portion 44 of each of the plurality of fluid delivery elements 8 such that the plurality of fluid delivery elements 8 are in the compressed and retracted position 80 to (ii) an expansion permitting position EPP of FIG. 4 in which the compression sheath 11 does not cover the hinge portion 44 of each of the plurality of fluid delivery elements 8 such that the plurality of fluid delivery elements 8 are in the naturally biased and expanded position 90.

The one or more needles 46 may be configured to penetrate a vessel wall of the vessel when in the naturally biased and expanded position 90 to deliver the therapeutic fluid to the vessel wall. It is to be understood, and as described herein, other embodiments of the catheter device 10 such as the catheter device 100 may operate in a similar manner with similar components to deliver therapeutic fluid through the lumens 54 of the needles 46 to a vessel. As described below, the catheter device 10 may include additional components.

Referring now to catheter device 100 of FIGS. 5-12, the catheter device 100 may further include a needle cover sheath 112 (FIG. 5) disposed over the compression sheath 111. In embodiments, the dual sheath coverage aids to provide additional structural support and safety when in the compressed and retracted position. The needle cover sheath 112 may be movable relative to the compression sheath 111, the guidewire tube 105 (FIG. 6), and the plurality of fluid delivery elements 108 extending to the hub 104 through the compression sheath 111. The hub 104 has a proximal end 124 and a distal end opposite the proximal end 126. The guidewire tube 105 may further include a tip 128, as described in greater detail below with respect to FIGS. 10-11.

Figure 5:
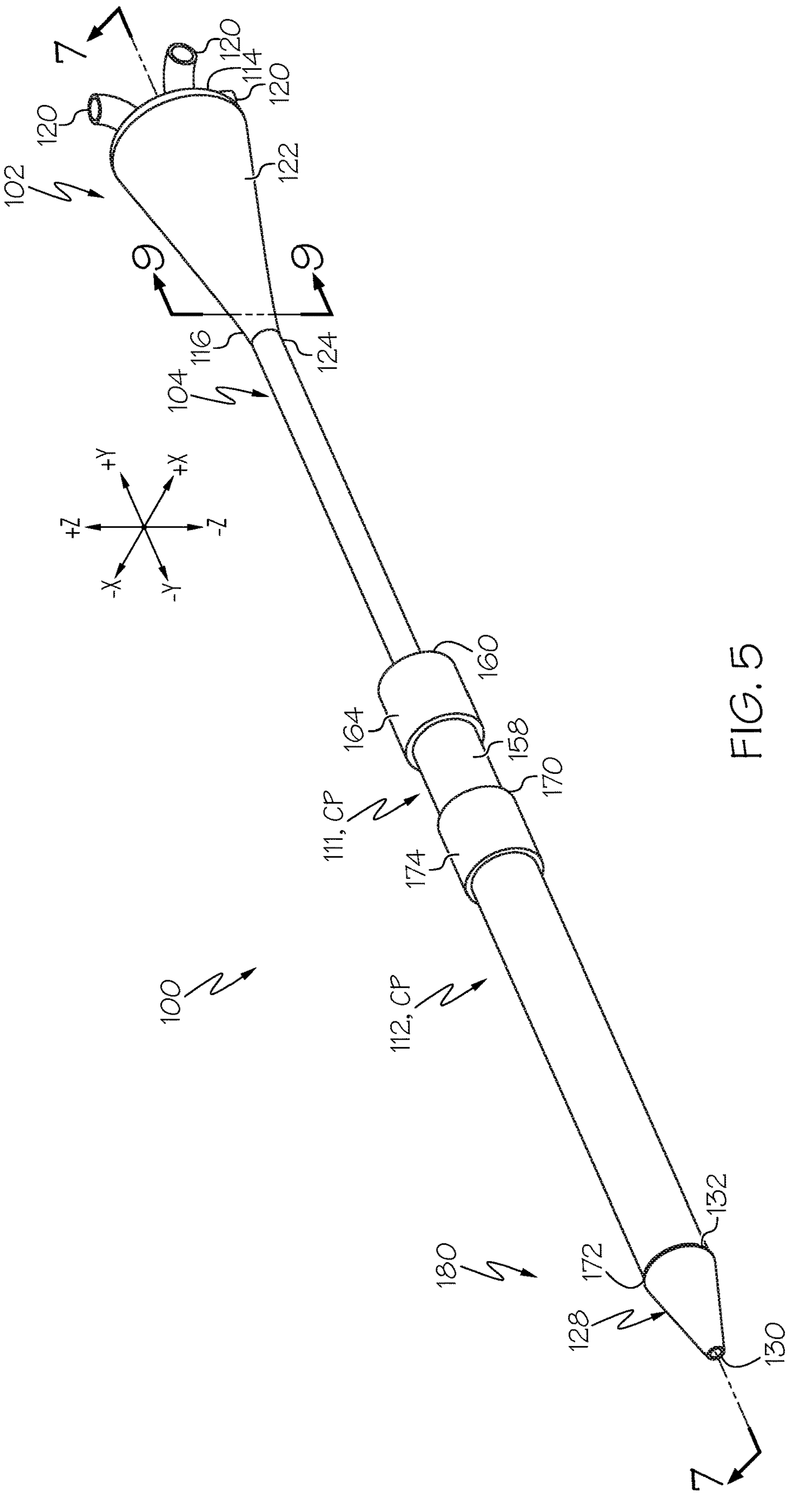
FIG. 5 schematically depicts a perspective view of another catheter device with a plurality of fluid delivery elements fully covered in a compressed and retracted position within a compression sheath, according to one or more embodiments shown and described herein.
Figure 6:
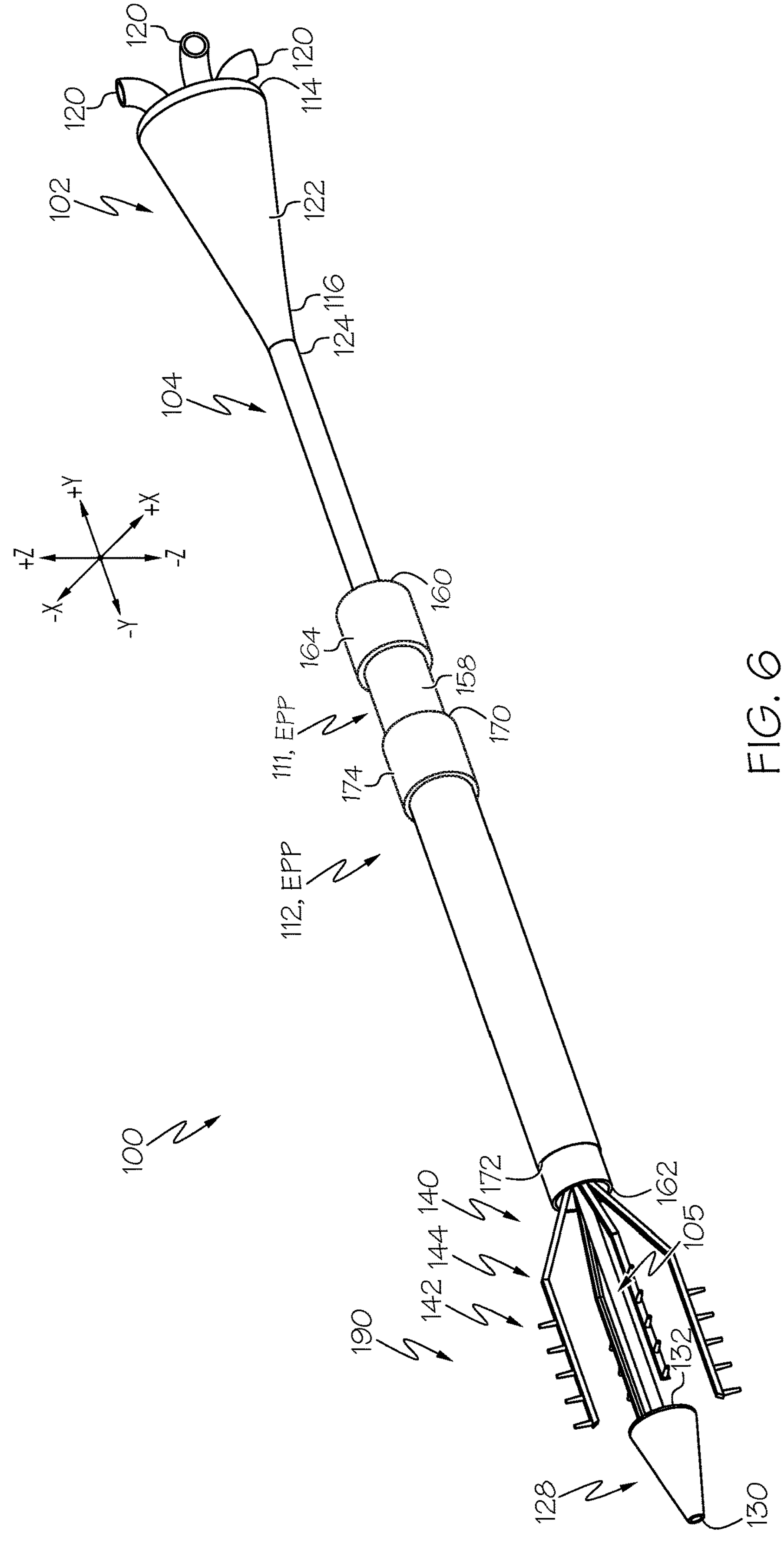
FIG. 6 schematically depicts a perspective view of the catheter device of FIG. 5 with the plurality of fluid delivery elements in a naturally biased and expanded position extending from the compression sheath.

FIG. 5 illustrates the catheter device 100 with the plurality of fluid delivery elements 108 fully covered in the compressed and retracted position 180 within the compression sheath 111 and the needle cover sheath 112, and FIG. 6 illustrates the catheter device 100 with the plurality of fluid delivery elements 108 in the naturally biased and expanded position 190 and extending from the compression sheath 111. As shown in FIGS. 5-6, the compression sheath 111 of the catheter device 100 may be moved distally away from the hub 104 to move from (i) the expansion permitting position EPP of FIG. 6 in which the compression sheath 111 does not cover the hinge portion 144 of each of the plurality of fluid delivery elements 108 such that the plurality of fluid delivery elements 108 are in the naturally biased and expanded position 190 to (ii) the covering position CP of FIG. 5 in which the compression sheath 111 covers the hinge portion 144 of each of the plurality of fluid delivery elements 108 such that the plurality of fluid delivery elements 108 are in the compressed and retracted position 180.

Figure 7:
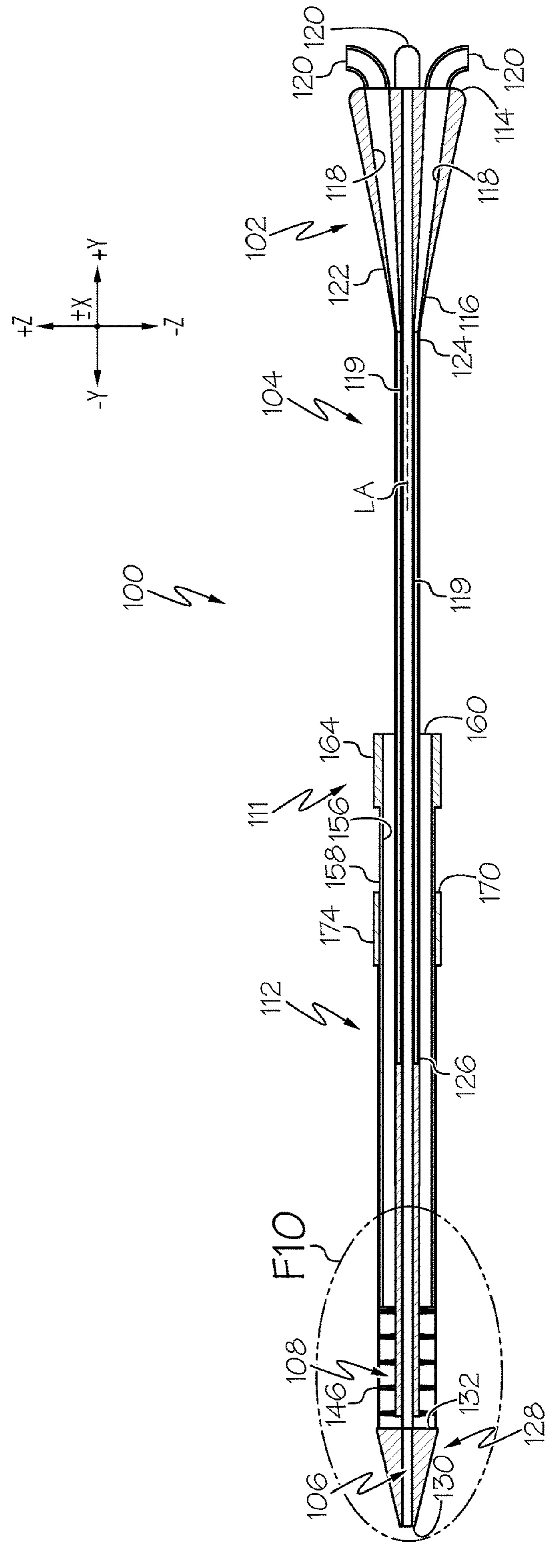
FIG. 7 schematically depicts a cross section view of the catheter device of FIG. 5 taken along line 7-7 of FIG. 5.
Figure 10:
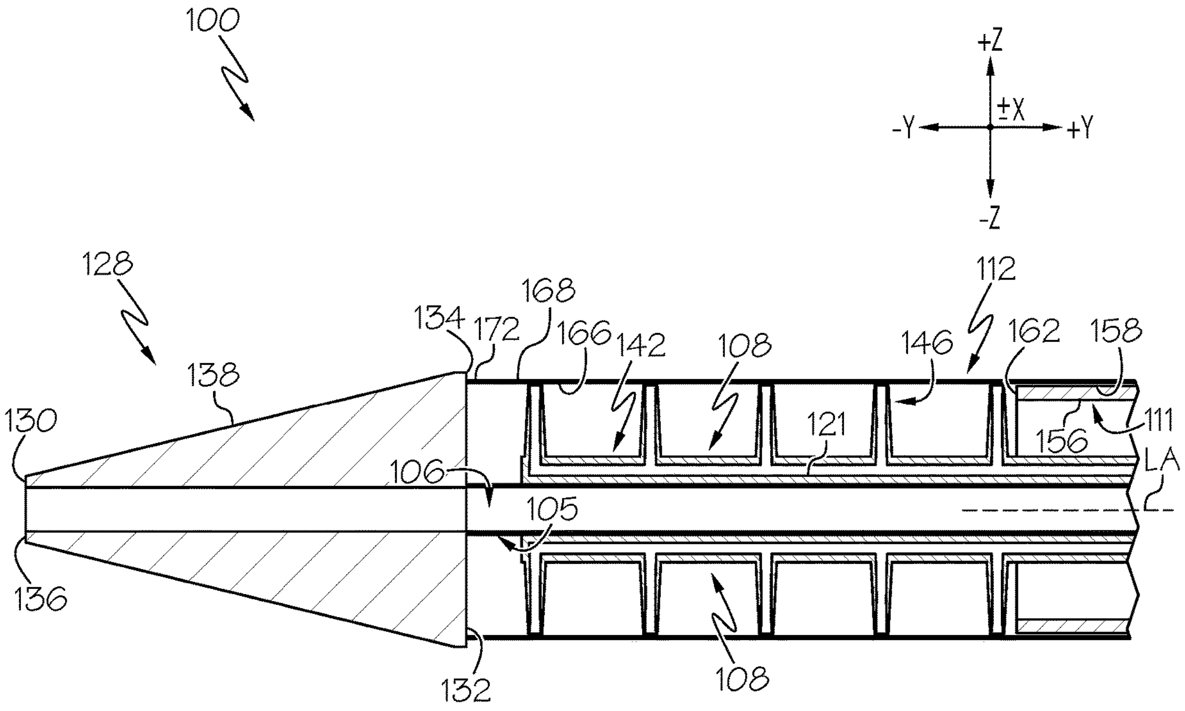
FIG. 10 schematically depicts an enlarged view of circle F10 of the catheter device of FIG. 7.

As shown in FIGS. 5-7, catheter device 100 may further include a proximal hub 102 distally connected to and in fluid communication with the hub 104, specifically, at the proximal end 124 of the hub 104. The proximal hub 102 includes a proximal end 114 and a distal end 116 opposite the proximal end 114. The guidewire tube 105, which defines a guidewire lumen 106 having the longitudinal axis LA extending along the +/−Y-axis of the coordinate axes, is coupled to the hub 104 and the proximal hub 102 via the hub 104. Further as shown in FIGS. 7 and 10, a fluid communication is formed between fluid delivery lumens 121 (FIG. 10) of each fluid delivery element 8, corresponding respective ports 119 of the hub 104 (FIG. 7), and corresponding respective fluid delivery lumens 118 (FIG. 7) of the proximal hub 102. The plurality of fluid delivery lumens 118 are formed in the proximal hub 102 and extends between the proximal end 114 and the distal end 116. A plurality of connections 120 are provided at the proximal end 114 of the proximal hub 102. Each connection 120 is in fluid communication with a fluid supply and a corresponding port 119 of the hub 104 to provide fluid to the respective fluid delivery lumens 118 from the fluid supplies through to the corresponding port 119 and further through to the corresponding fluid delivery lumen 121 of the fluid delivery element 8 and the corresponding needle lumen 54 of the needle 46 of the respective fluid delivery element 8. The fluid supplies may store any suitable therapeutic fluid such as, for example, Paclitaxel® or another antiproliferative agent, Sirolimus®, a corticosteroid such as dexamethasone, a contrast agent for visualization, and the like. It should be appreciated that each fluid delivery lumen 118, may be in fluid communication with a different fluid supply to provide a different fluid to each fluid delivery lumen 118. Thus, one or more of the fluid delivery elements 108 may provide one or more different fluids via respective needle lumens 54 as provided by corresponding fluid delivery lumens 118. Alternatively, more than one of the connections 120 may be in fluid communication with the same fluid supply to provide the same fluid to more than one fluid delivery lumen 118. Thus, one or more of the fluid delivery elements 108 may provide one or more same fluids via respective needle lumens 54 as provided by corresponding fluid delivery lumens 118. The connections 120 may connect to the associated fluid supplies in any suitable manner. For example, the connections 120 may each include a luer connection for connecting each connection 120 to an associate fluid supply.

Referring still to FIGS. 5-7, in embodiments, the proximal hub 102 includes an outer surface 122 having a diameter at the proximal end 114 of the proximal hub 102 that is greater than a diameter of the outer surface 122 at the distal end 116 of the proximal hub 102. Thus, each fluid delivery lumen 18 may have a diameter at the proximal end 114 of the proximal hub 102 that is greater than a diameter of each fluid delivery lumen 118 at the distal end 116 of the proximal hub 102 (e.g., the proximal hub 102 is tapered). However, as shown, the diameter of the guidewire tube 105 within the proximal hub 102 may remain constant. The proximal hub 102 being tapered may aid to concentrate the fluid flow within the proximal hub 102 to increase rate of flow of the fluid through the fluid delivery lumens 118 while allowing for connections 120 to have a larger diameter, as discussed herein. In other embodiments, the outer surface 122 of the proximal hub 102 may not be tapered. In such a non-tapered embodiment, the diameter of each fluid delivery lumen 118 at the proximal end 114 of the proximal hub 102 may be equal to the diameter of each fluid delivery lumen 118 at the distal end 116 of the proximal hub 102 and the diameter of each fluid delivery lumen 118 may remain constant. In some embodiments, the proximal hub 102 may be tapered and the diameter of each fluid delivery lumen 118 at the proximal end 114 of the proximal hub 102 may be equal to the diameter of each fluid delivery lumen 118 at the distal end 116 of the proximal hub 102 and the diameter of each fluid delivery lumen 118 may remain constant. In embodiments, the proximal hub 102 is formed from a thermoplastic polymer such as, for example, polycarbonate.

In the embodiments of the catheter device 10 of FIGS. 5-7, with respect to the compression sheath 111, the compression sheath 111 has an inner surface 156 and an outer surface 158 opposite the inner surface 156. The compression sheath 111 also has a proximal end 160, a distal end 162 opposite the proximal end 160, and a compression sheath hub 164 provided at or near the proximal end 160 of the compression sheath 111. With respect now to the needle cover sheath 112, the needle cover sheath 112 has an inner surface 166 and an outer surface 168 opposite the inner surface 166. The needle cover sheath 112 surrounds the compression sheath 111 such that the inner surface 166 of the needle cover sheath 112 faces the outer surface 158 of the compression sheath 111. The needle cover sheath 112 also has a proximal end 170, a distal end 172 opposite the proximal end 170, and a needle cover sheath hub 174 provided at or near the proximal end 170 of the needle cover sheath 112.

Figure 8:
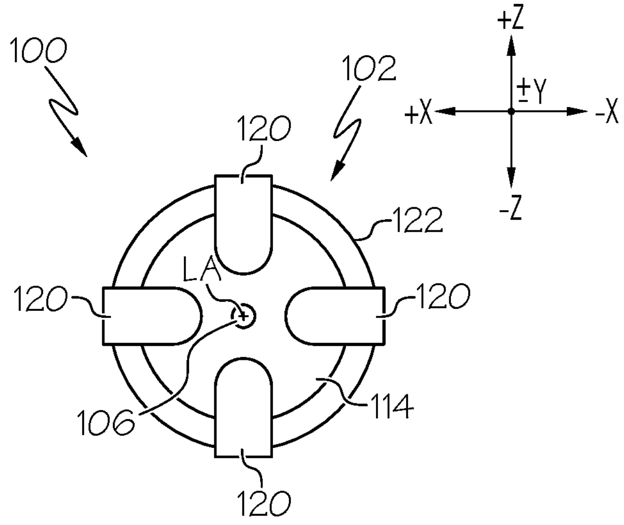
FIG. 8 schematically depicts a proximal to distal view of the catheter device of FIG. 5.
Figure 9:
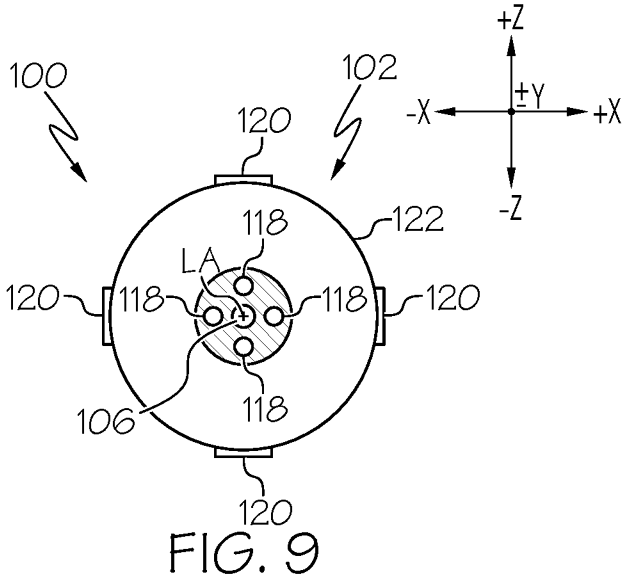
FIG. 9 schematically depicts a cross-section distal to proximal view of the catheter device of FIG. 5 taken along line 9-9 of FIG. 5.

Referring now to FIGS. 8 and 9, as a non-limiting example, the proximal hub 102 is depicted as including four connections 120 (e.g., which connections 120 are configured to couple to fluid sources such as to receive fluid) with each connection 120 (FIG. 8) associated with a corresponding fluid delivery lumen 118 (FIG. 9). As such, the proximal hub 102 as shown includes four fluid delivery lumens 118 formed therein. However, it should be understood that the present disclosure is not limited to this specific number of fluid delivery lumens 118. For example, the proximal hub 102 may include a greater or fewer number of fluid delivery lumens 118.

The connections 120 are each shown extending radially away from the guidewire tube 105. However, in embodiments, it should be appreciated that the connections 120 may extend parallel to the guidewire tube 105 and along the longitudinal axis LA. In addition, as shown in FIG. 9, the guidewire tube 105 is shown formed in the proximal hub 102 with the plurality of fluid delivery lumens 118 equidistantly spaced apart from one another and disposed about the longitudinal axis LA of the guidewire tube 105. Similarly, as shown in FIG. 8, the connections 120 are equidistantly spaced apart from one another at the proximal end 114 of the proximal hub 102 to be aligned and in fluid communication with the fluid delivery lumens 118. However, it should be appreciated that other configurations are contemplated. For example, the fluid delivery lumens 118 may be located substantially on one side of the guidewire tube 105.

Figure 11:
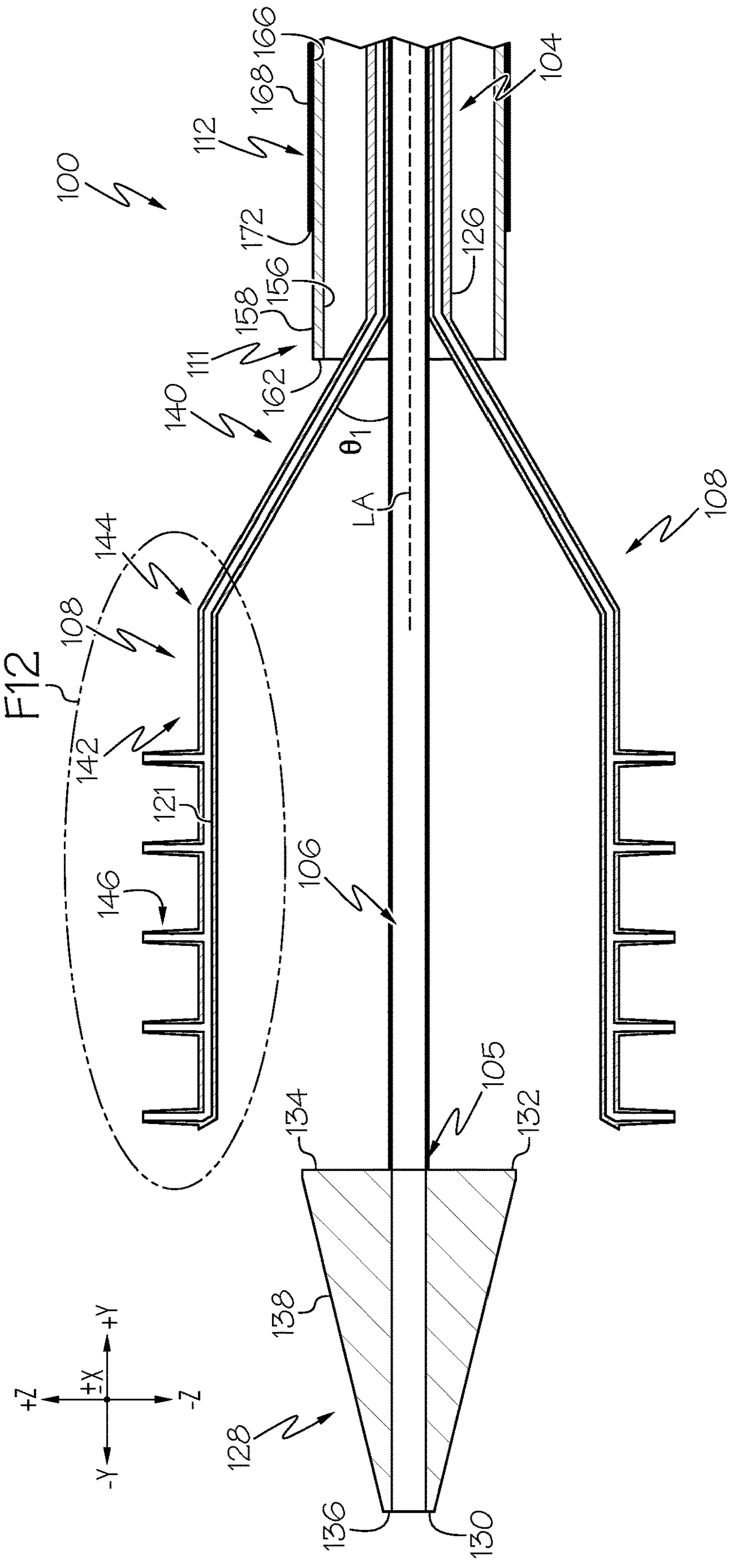
FIG. 11 schematically depicts a partial cross-section view of the catheter device of FIG. 6 with the plurality of fluid delivery elements in the naturally biased and expanded position extending from the compression sheath.

Referring now to FIGS. 10 and 11, the guidewire tube 105 is shown in greater and enlarged detail as extending from the distal end 126 (FIG. 7) of the hub 104 along the longitudinal axis LA. The guidewire tube 105 includes the tip 128 provided at the distal end 130 of the guidewire tube 105. The tip 128 may aid to act as a distal guide and a stop against which each fluid delivery element 108 may rest in the compressed and retracted position to provide additional cover. The tip 128 includes the proximal end 132 having the proximal tip circumference 134 and a distal end 136 opposite the proximal end 132. A diameter of the proximal end 132 of the tip 128 defining the proximal tip circumference 134 is greater than a diameter of the distal end 136 of the tip 128. Accordingly, an outer surface 138 of the tip 128 tapers from the proximal end 132 of the tip 128 to the distal end 136 of the tip 128 forming a tapered distal end 136. The top 128 being tapered facilitates navigation of the catheter device 100 when in use. In embodiments, the tip 128 (and/or any other components of the catheter 10, 100) is formed from any suitable polymer such as, for example, nylon, Pebax®, and the like.

Additionally, as shown in FIGS. 10 and 11, a plurality of fluid delivery elements 108 is shown extending from the distal end 126 of the hub 104, which extends from the proximal hub 102. Each fluid delivery lumen 118 extends through the proximal hub 102 to be in respective fluid communication with a respective port 119 of the hub 104, a respective fluid delivery lumen 121 of a respective fluid delivery element 108, and a respective needle lumen 154 of the respective fluid delivery element 108. As described herein, and shown in greater and enlarged detail in FIGS. 10-11, each fluid delivery element 108 respectively includes a proximal portion 140, a distal portion 142, and a hinge portion 144 provided between the proximal portion 140 and the distal portion 142. It should be appreciated that the proximal portion 140 of each fluid delivery element 108 extends from the distal end 126 of the hub 104. Thus, the fluid delivery lumens 118 and associated ports 119, which extend through the hub 104, are fluidly coupled to corresponding fluid delivery lumens 121 of each respective fluid delivery element 108, which fluid delivery lumens 121 extend through the proximal portion 140, the distal portion 142, and the hinge portion 144 of each fluid delivery element 108. In addition, as described herein, each fluid delivery element 108 includes one or more needles 146 provided on the distal portion 142 of the fluid delivery element 108 and extend in a direction perpendicular to the longitudinal axis LA of the guidewire lumen 106.

As shown, each fluid delivery element 108 may include a plurality of needles 146. In FIGS. 10-11, each fluid delivery element 108 is shown as including five needles 146. However, it should be appreciated that each fluid delivery element 108 may include any suitable number of needles 146 such as less than five or more than five. Moreover, the fluid delivery elements 108 need not include the same number of needles 146. For example, one or more of the fluid delivery elements 108 may include a first number of needles 146, and another one or more of the fluid delivery elements 108 may include a second number of needles 146 greater than or less than the first number of needles 146. In embodiments, the needles 146 may be formed from any suitable material such as, for example, silicon, Nitinol®, stainless steel, nickel, and the like.

Figure 12:
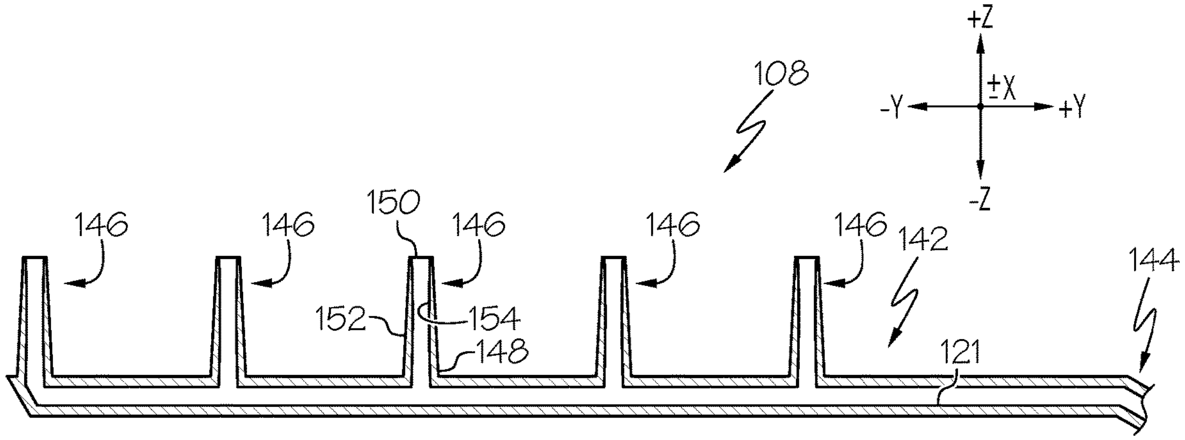
FIG. 12 schematically depicts an enlarged view of circle F12 of the catheter device of FIG. 11.

Referring now to FIG. 12, an enlarged partial view of one of the fluid delivery elements 108 is shown. Each needle 146 includes a proximal end 148 and a distal end 150 opposite the proximal end 148. The needles 146 extend from the distal portion 142 of the fluid delivery element 108 and connect to the distal portion 142 at the proximal end 148 of each needle 146. Each needle 146 has an outer surface 152 that tapers from the proximal end 148 to the distal end 150 to facilitate puncturing into a vessel wall of a vessel. A needle lumen 154 is formed within each needle 146 and each needle lumen 154 is in fluid communication with a corresponding fluid delivery lumen 121 extending through the proximal portion 140, the distal portion 142, and the hinge portion 144 of the fluid delivery elements 108. Despite the outer surface 152 of each needle 146 being tapered, in embodiments, a diameter of the needle lumen 154 may remain constant. Accordingly, as shown in FIG. 12, five needle lumens 154, with each needle lumen 154 formed within a corresponding needle 146, are shown in fluid communication with a single fluid delivery lumen 121 formed within a corresponding fluid delivery element 108. Thus, each needle lumen 154 associated with a corresponding fluid delivery element 108 is in fluid communication with a corresponding fluid supply that supplies fluid to that particular fluid delivery lumen 121 as described herein.

As described in more detail herein, the fluid delivery elements 108 are at least partially formed from a naturally biasing material that causes the fluid delivery elements 108 to flex radially outwardly from the longitudinal axis LA of the guidewire lumen 106. In embodiments, the fluid delivery elements 108 are formed from any suitable material such as, for example, silicon, or Nitinol®, stainless steel, and the like, to provide the necessary biasing effect. In embodiments, the hinge portion 144 of the fluid delivery elements 108 and the manner in which the proximal portion 140 of the fluid delivery elements 108 is joined to the distal end 126 of the hub 104 results in the fluid delivery elements 108 naturally biasing radially away from the guidewire tube 105 while allowing the distal portion 142 of the fluid delivery elements 108 to remain in alignment with, i.e., at a parallel orientation relative to, the longitudinal axis LA of the guidewire lumen 106. As such, the fluid delivery elements 108 are positionable between a compressed and retracted position 180, as shown in FIG. 10, and a naturally biased and expanded position 190, as shown in FIG. 11. In embodiments, the hinge portion 144 may include additional or alternative biasing components such as leaf springs or the like to move between the compressed and retracted position 180 when covered to the naturally biased and expanded position 190 as described herein. It should be appreciated that the hinge portion 144 is formed by the joining of the proximal portion 140 and the distal portion 142 of the fluid delivery elements 108 without preventing fluid flow through the hinge portion 144. In embodiments, the hinge portion 144 may be integrally formed as a one piece, monolithic structure with the proximal portion 140 and the distal portion 142 of the fluid delivery elements 108 without providing any separate structure.

When the fluid delivery elements 108 are in the compressed and retracted position 180 and are covered, as shown in FIG. 10, the proximal portion 140 and the distal portion 142 of the fluid delivery elements 108 may both be oriented parallel, or at least substantially parallel, to the longitudinal axis LA of the guidewire lumen 106. Thus, the needles 146, and more particularly the distal end 150 of the needles 146, are disposed within the proximal tip circumference 134 of the tip 128 of the guidewire tube 105. Alternatively, when the fluid delivery elements 108 are in the naturally biased and expanded position 190 and are uncovered, as shown in FIG. 11, the proximal portion 140 of the fluid delivery elements 108 extends from the distal end 126 of the hub 104 at an angle so that the proximal portion 140 of the fluid delivery elements 108 is not aligned with, i.e., does not extend parallel to, the longitudinal axis LA of the guidewire lumen 106. For example, the proximal portion 140 of the fluid delivery element 108 extends from a longitudinal axis of the hub 104 at a first angle $\theta_1$ greater than or equal to 10 degrees and less than or equal to 80 degrees. In embodiments, the first angle $\theta_1$ is greater than or equal to 20 degrees and less than or equal to 70 degrees. In embodiments, the first angle $\theta_1$ is greater than or equal to 30 degrees and less than or equal to 60 degrees, the first angle $\theta_1$ is greater than or equal to 40 degrees and less than or equal to 50 degrees. Thus, when the fluid delivery elements 108 are in the naturally biased and expanded position 190, the needles 146, and more particularly the distal end 150 of the needles 146, are disposed outside of the proximal tip circumference 134 of the tip 128. However, as shown, the distal portion 142 of the fluid delivery elements 108 may remain substantially aligned with and parallel to the longitudinal axis LA of the guidewire lumen 106. To permit the proximal portion 140 of the fluid delivery elements 108 to extend from the distal end 126 of the hub 104 at an angle, a similar hinge portion, similar to the hinge portion 144, may be provided at the joining of the fluid delivery elements 108 and the hub 104.

As used herein, reference to the distal end 150 of the needles 146 being "within" the proximal tip circumference 134 refers the distal end 150 of a particular needle 146 being positioned further from the longitudinal axis LA of the guidewire lumen 106 in the +/−Z direction as compared to an outermost point of the proximal end 132 of the tip 128. Similarly, reference to the distal end 150 of the needles 146 being "outside" of the proximal tip circumference 134 refers the distal end 150 of a particular needle 146 being positioned closer to the longitudinal axis LA of the guidewire lumen 106 in the +/−Z direction as compared to the outermost point of the proximal end 132 of the tip 128.

Referring to FIGS. 7 and 10-11, the compression sheath 111 and the needle cover sheath 112 are shown disposed around a portion of the hub 104, which extends from the distal end 116 of the proximal hub 102. Specifically, the compression sheath 111 is shown moved along the longitudinal axis LA relative to the hub 104 in a distal direction opposite the proximate end 114 of the proximal hub 102 to be in the covering position CP. Additionally, the needle cover sheath 112 is shown moved along the longitudinal axis LA relative to the hub 104 in a distal direction opposite the proximal end 114 of the hub 104 to be in the covering position CP as well.

The compression sheath hub 164 facilitates positioning of the compression sheath 111 between the covering position CP, as shown in FIG. 10, and the expansion permitting position EPP, as shown in FIG. 11. When in the covering position CP, the compression sheath 111 extends over the proximal portion 140 and the hinge portion 144 of each of the fluid delivery elements 108. In embodiments, the compression sheath 111 extends partially over the distal portion 142 of the fluid delivery elements 108 when the compression sheath 111 is in the covering position CP. As shown in FIG. 10, the compression sheath 111 may have an outer diameter less than a diameter between the distal end 150 of diametrically opposing needles 146 on opposite sides of the guidewire tube 105. Accordingly, with the compression sheath 111 in the covering position CP, the compression sheath 111 is not permitted to extend over the needles 146.

As discussed in more detail herein, the compression sheath 111 is operated to permit the fluid delivery elements 108 to move between the compressed and retracted position 180, and the naturally biased and expanded position 190. With the compression sheath 111 in the covering position CP, the compression sheath 111 compresses the fluid delivery elements 108 so that the fluid delivery elements 108 are maintained in the compressed and retracted position 180. However, once the compression sheath 111 is moved to the expansion permitting position EPP, the fluid delivery elements 108 are permitted to move to the naturally biased and expanded position 190, assuming the needle cover sheath 112 is also in the expansion permitting position EPP, as discussed herein.

The needle cover sheath hub 174 of the needle cover sheath 112 facilitates positioning of the needle cover sheath 112 between the covering position CP, as shown in FIG. 10, and an expansion permitting position EPP, as shown in FIG. 11. When in the covering position CP, the needle cover sheath 112 extends over the proximal portion 140 of each of the fluid delivery elements 108. However, in embodiments, the needle cover sheath 112 also extends over the hinge portion 144 and the distal portion 142 when in the covering position CP. As shown in FIG. 10, the needle cover sheath 112 has an outer diameter greater than a diameter between the distal end 150 of diametrically opposing needles 146 on opposite sides of the guidewire tube 105. Accordingly, with the needle cover sheath 112 in the covering position CP, the needle cover sheath 112 extends over each of the needles 146. In embodiments, as shown in FIGS. 5 and 10, the distal end 172 of the needle cover sheath 112 is configured to abut against the tip 128, such as against the proximal end 132 of the tip 128, when the plurality of fluid delivery elements 108 are in the compressed and retracted position 180 (FIG. 5) and disposed within the proximal tip circumference 134 (FIG. 10) of the proximal end 132 of the tip 128. In embodiments, and as shown in FIG. 6, the distal end 172 of the needle cover sheath 112 is configured to be spaced away from the tip 128 when the plurality of fluid delivery elements 108 are in the naturally biased and expanded position 190 and disposed exterior to the proximal tip circumference 134 (FIG. 10) of the proximal end 132 of the tip 128.

As discussed in more detail herein, the needle cover sheath 112 is operated to conceal the fluid delivery elements 108 while navigating the catheter device 100 to prevent incidental puncturing by the needles 146. Specifically, when the needle cover sheath 112 is in the covering position, the needles 146 of the fluid delivery elements 108 are concealed, and when the needle cover sheath 112 is in the expansion permitting position EPP, the needles 146 are exposed. As such, without the needle cover sheath 12, the fluid delivery elements 108 would remain exposed and may result in incidental puncturing by the needles 146 and/or leakage of fluid out of the needles 146.

In use, the compression sheath 111 and the needle cover sheath 112 may both be in the covering position CP and the fluid delivery elements 108 are maintained in the compressed and retracted position 180. A guidewire may then be navigated through the guidewire lumen 106 of the guidewire tube 105 and the catheter device 100 be positioned at an injection site. The tip 128 of the catheter device 100 being tapered may assist in maneuvering the catheter device 100 toward the injection site. Once positioned at the injection site, the compression sheath 111 and the needle cover sheath 112 may be proximally moved relative to the guidewire tube 105 and the fluid delivery elements 108 toward the proximal hub 102. The compression sheath 111 and the needle cover sheath 112 may be moved from the covering position CP, in which the needles 146 of the fluid delivery elements 108 are covered by the needle cover sheath 112, to the expansion permitting position EPP by gripping the compression sheath hub 164 and the needle cover sheath hub 174 and manually drawing the compression sheath 111 and the needle cover sheath 112 proximally toward the proximal hub 102. The compression sheath 111 and the needle cover sheath 112 may be moved into the expansion permitting position either simultaneously or sequentially. For example, the compression sheath 111 may be initially drawn toward the proximal hub 102 and positioned into the expansion permitting position EPP and, subsequently, the needle cover sheath 112 may be drawn toward the proximal hub 102.

In any event, once the compression sheath 111 and the needle cover sheath 112 are both moved into the expansion permitting position EPP, the fluid delivery elements 108 are permitted to move into the naturally biased and expanded position 190 such that each of the fluid delivery elements 108 radially extend from the longitudinal axis LA of the guidewire lumen 106 to allow the needles 146 to penetrate a vessel wall of a vessel or other member to be injected with fluid. As referred to herein, "naturally biased" refers to the fluid delivery elements 108 being configured to automatically move into the naturally biased and expanded position 190 once the compression sheath 111 is moved into the expansion permitting position EPP without any additional action required by a user. As discussed herein, this is due to the fluid delivery elements 108 being at least partially formed from a naturally biasing material that causes the fluid delivery elements 108 to flex radially outwardly from the longitudinal axis LA of the guidewire lumen 106. Thereafter, fluid from each of the fluid supplies is delivered to the ports 119, which is subsequently delivered to the needles 146 of each fluid delivery element 108 via the fluid delivery lumens 121 and the needle lumens 154. Once the desired amount of fluid is delivered, the compression sheath 111 is moved toward the tip 128 and toward the covering position CP such that the distal end 162 of the compression sheath 111 contacts the proximal portion 140 of the fluid delivery elements 108 and compresses the fluid delivery elements 108 back into the compressed and retracted position 180. Thereafter, the needle cover sheath 112 may then be moved toward the tip 128 and into the covering position CP to cover the needles 146 of the fluid delivery elements 108 and prevent additional fluid from exiting the needles 146.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about." it will be understood that the particular value forms another embodiment. It will be further understood that the endpoints of each of the ranges are significant both in relation to the other endpoint, and independently of the other endpoint.

Directional terms as used herein—for example up, down, right, left, front, back, top, bottom—are made only with reference to the figures as drawn and are not intended to imply absolute orientation.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a." "an" and "the" include plural referents unless the context clearly dictates otherwise. Thus, for example, reference to "a" component includes aspects having two or more such components, unless the context clearly indicates otherwise.

Embodiments may be further described with reference to the following numbered clauses:

1. A catheter device comprising: a hub including a plurality of ports, each port of the plurality of ports configured to receive a fluid; a guidewire tube extending from the hub and defining a guidewire lumen comprising a longitudinal axis; a plurality of fluid delivery elements extending from the hub and disposed about the guidewire tube, each fluid delivery element of the plurality of fluid delivery elements including a proximal portion, a distal portion, a hinge portion therebetween, and one or more needles on the distal portion extending in a direction perpendicular to the longitudinal axis of the guidewire lumen, a distal end of each fluid delivery element configured to adjust between (i) a naturally biased and expanded position at a spaced distance from the guidewire tube in which the proximal portion is angled with respect to the distal portion via the hinge portion and (ii) a compressed and retracted position abutting the guidewire tube in which the proximal portion is in alignment with the distal portion; and a compression sheath disposable over and slidably movable relative to the plurality of fluid delivery elements, wherein the plurality of fluid delivery elements are naturally biased in the naturally biased and expanded position when the compression sheath is proximally disposed in an expansion permitting position in which the compression sheath does not cover the hinge portion of each of the plurality of fluid delivery elements, and wherein the plurality of fluid delivery elements are in the compressed and retracted position when the compression sheath is distally disposed in a covering position in which the compression sheath covers the hinge portion of each of the plurality of fluid delivery elements.

2. The catheter device of clause 1, wherein each needle of the one or more needles on a respective fluid delivery element comprises a needle lumen that is in fluid communication with a corresponding port of the plurality of ports of the hub through a corresponding fluid delivery lumen of the respective fluid delivery element of the plurality of fluid delivery elements.

3. The catheter device of clause 1 or clause 2, wherein each needle of the one or more needles includes a taper at a distal end of the needle, the distal end of the needle being spaced away and extending in a direction facing away from the guidewire tube.

4. The catheter device of any one of clauses 1-3, further comprising a needle cover sheath disposed over the compression sheath, the needle cover sheath movable relative to the compression sheath, the guidewire tube, and the plurality of fluid delivery elements extending to the hub through the compression sheath.

5. The catheter device of clause 4, wherein the guidewire tube further comprises a tip at a distal end of the guidewire tube, the tip comprises a proximal end having a proximal tip circumference and a tapered distal end, a distal end of the needle cover sheath configured to abut the tip when the plurality of fluid delivery elements are in the compressed and retracted position and disposed within the proximal tip circumference, and the distal end of the needle cover sheath configured to be spaced away from the tip when the plurality of fluid delivery elements are in the naturally biased and expanded position and disposed exterior to the proximal tip circumference.

6. The catheter device of any one of clauses 1-5, wherein the plurality of fluid delivery elements comprises at least two fluid delivery elements spaced apart on a shared plane.

7. The catheter device of any one of clauses 1-6, wherein the plurality of fluid delivery elements comprises at least four fluid delivery elements, each of the plurality of fluid delivery elements are equidistantly spaced apart from one another.

8. A catheter device comprising: a hub including a plurality of ports, each port of the plurality of ports configured to receive a fluid; a guidewire tube extending from the hub and defining a guidewire lumen comprising a longitudinal axis; a plurality of fluid delivery elements extending from the hub and disposed about the guidewire tube, each fluid delivery element of the plurality of fluid delivery elements including a proximal portion, a distal portion, a hinge portion therebetween, and one or more needles on the distal portion extending in a direction perpendicular to the longitudinal axis of the guidewire lumen, a distal end of each fluid delivery element configured to adjust between (i) a naturally biased and expanded position at a spaced distance from the guidewire tube in which the proximal portion is angled with respect to the distal portion via the hinge portion and (ii) a compressed and retracted position abutting the guidewire tube in which the proximal portion is in alignment with the distal portion; and a compression sheath disposable over and slidably movable relative to the plurality of fluid delivery elements; wherein the plurality of fluid delivery elements are naturally biased in the naturally biased and expanded position when the compression sheath is proximally disposed in an expansion permitting position in which the compression sheath does not cover the hinge portion of each of the plurality of fluid delivery elements, and wherein the plurality of fluid delivery elements are in the compressed and retracted position when the compression sheath is distally disposed in a covering position in which the compression sheath covers the hinge portion of each of the plurality of fluid delivery elements, wherein each needle of the one or more needles on a respective fluid delivery element comprises a needle lumen that is in fluid communication with a corresponding port of the plurality of ports of the hub through a corresponding fluid delivery lumen of the respective fluid delivery element of the plurality of fluid delivery elements, and each needle of the one or more needles includes a taper at a distal end of the needle.

9. The catheter device of clause 8, wherein the distal end of the needle is spaced away and extending in a direction facing away from the guidewire lumen.

10. The catheter device of clause 8 or clause 9, further comprising a needle cover sheath disposed over the compression sheath, the needle cover sheath movable relative to the compression sheath, the guidewire tube, and the plurality of fluid delivery elements extending to the hub through the compression sheath, wherein the guidewire tube further comprises a tip at a distal end of the guidewire tube, the tip comprises a proximal end having a proximal tip circumference and a tapered distal end, a distal end of the needle cover sheath configured to abut the tip when the plurality of fluid delivery elements are in the compressed and retracted position and disposed within the proximal tip circumference, and the distal end of the needle cover sheath configured to be spaced away from the tip when the plurality of fluid delivery elements are in the naturally biased and expanded position and disposed exterior to the proximal tip circumference.

11. The catheter device of any one of clauses 8-10, wherein the plurality of fluid delivery elements comprises at least two fluid delivery elements intersecting and spaced apart on a shared plane.

12. The catheter device of any one of clauses 8-11, wherein the plurality of fluid delivery elements comprises at least four fluid delivery elements, each of the plurality of fluid delivery elements are equidistantly spaced apart from one another.

13. A method of delivering a therapeutic fluid to a vessel, the method comprising: positioning a catheter device within the vessel, the catheter device comprising: a hub including a plurality of ports, each port of the plurality of ports configured to receive a fluid; a guidewire tube extending from the hub and defining a guidewire lumen comprising a longitudinal axis; a plurality of fluid delivery elements extending from the hub and disposed about the guidewire tube, each fluid delivery element of the plurality of fluid delivery elements including a proximal portion, a distal portion, a hinge portion therebetween; and one or more needles on the distal portion extending in a direction perpendicular to the longitudinal axis of the guidewire lumen, a distal end of each fluid delivery element configured to adjust between (i) a naturally biased and expanded position at a spaced distance from the guidewire tube in which the proximal portion is angled with respect to the distal portion via the hinge portion and (ii) a compressed and retracted position abutting the guidewire tube in which the proximal portion is in alignment with the distal portion, and a compression sheath disposable over and slidably movable relative to the plurality of fluid delivery elements; and moving the compression sheath of the catheter device proximally toward the hub to move from (i) a covering position in which the compression sheath covers the hinge portion of each of the plurality of fluid delivery elements such that the plurality of fluid delivery elements are in the compressed and retracted position to (ii) an expansion permitting position in which the compression sheath does not cover the hinge portion of each of the plurality of fluid delivery elements such that the plurality of fluid delivery elements are in the naturally biased and expanded position.

14. The method of clause 13, further comprising the one or more needles penetrating a vessel wall of the vessel when in the naturally biased and expanded position.

15. The method of clause 13 or clause 14, wherein each needle of the one or more needles on a respective fluid delivery element comprises a needle lumen that is in fluid communication with a corresponding port of the plurality of ports of the hub through a corresponding lumen of the respective fluid delivery element of the plurality of fluid delivery elements, and further comprising delivering the therapeutic fluid from the hub through the plurality of ports of the hub through a corresponding fluid delivery lumen of each of the plurality of fluid delivery elements and through a corresponding needle lumen of each needle of the one or more needles.

16. The method of any one of clauses 13-15, further comprising moving the compression sheath of the catheter device distally away from the hub to move from (i) the expansion permitting position in which the compression sheath does not cover the hinge portion of each of the plurality of fluid delivery elements such that the plurality of fluid delivery elements are in the naturally biased and expanded position to (ii) the covering position in which the compression sheath covers the hinge portion of each of the plurality of fluid delivery elements such that the plurality of fluid delivery elements are in the compressed and retracted position.

17. The method of any one of clauses 13-16, wherein each needle of the one or more needles includes a taper at a distal end of the needle, the distal end of the needle being spaced away and extending in a direction facing away from the guidewire tube.

18. The method of any one of clauses 13-17, wherein the plurality of fluid delivery elements comprises at least four fluid delivery elements, each of the plurality of fluid delivery elements are equidistantly spaced apart from one another.

19. The method of any one of clauses 13-18, wherein the catheter device further comprises a needle cover sheath disposed over the compression sheath, the needle cover sheath movable relative to the compression sheath, the guidewire lumen, and the plurality of fluid delivery elements extending to the hub through the compression sheath.

20. The method of any one of clauses 13-19, wherein the guidewire tube further comprises a tip at a distal end of the guidewire tube, the tip comprises a proximal end having a proximal tip circumference and a tapered distal end, a distal end of the needle cover sheath configured to abut the tip when the plurality of fluid delivery elements are in the compressed and retracted position and disposed within the proximal tip circumference, and the distal end of the needle cover sheath configured to be spaced away from the tip when the plurality of fluid delivery elements are in the naturally biased and expanded position and disposed exterior to the proximal tip circumference.

From the above, it is to be appreciated that defined herein is catheter device including a hub, a multilumen shaft extending from the hub, a guidewire lumen extending from the multilumen shaft opposite the hub, a plurality of fluid delivery elements extending from the multilumen shaft opposite the hub, a compression sheath disposable over and slidably movable relative to the plurality of fluid delivery elements, and a needle cover sheath surrounding the compression sheath and movable relative to the fluid delivery elements. The fluid delivery elements are configured to adjust between a naturally biased and expanded position at a spaced distance from the guidewire lumen, and a compressed and retracted position abutting the guidewire lumen.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A catheter device comprising:

a hub including a plurality of ports, each port of the plurality of ports configured to receive a fluid;

a guidewire tube extending from the hub and defining a guidewire lumen comprising a longitudinal axis;

a plurality of fluid delivery elements extending from the hub and disposed about the guidewire tube, each fluid delivery element of the plurality of fluid delivery elements including a proximal portion, a distal portion, a hinge portion therebetween, and one or more needles on the distal portion extending in a direction perpendicular to the longitudinal axis of the guidewire lumen, a distal end of each fluid delivery element configured to adjust between (i) a naturally biased and expanded position at a spaced distance from the guidewire tube in which the proximal portion is angled with respect to the distal portion via the hinge portion and (ii) a compressed and retracted position abutting the guidewire tube in which the proximal portion is in alignment with the distal portion;

a compression sheath disposable over and slidably movable relative to the plurality of fluid delivery elements; and a needle cover sheath disposed over the compression sheath, the needle cover sheath movable relative to the compression sheath, the guidewire tube, and the plurality of fluid delivery elements extending to the hub through the compression sheath, wherein the plurality of fluid delivery elements are naturally biased in the naturally biased and expanded position when the compression sheath is proximally disposed in an expansion permitting position in which the compression sheath does not cover the hinge portion of each of the plurality of fluid delivery elements, and wherein the plurality of fluid delivery elements are in the compressed and retracted position when the compression sheath is distally disposed in a covering position in which the compression sheath covers the hinge portion of each of the plurality of fluid delivery elements.

2. The catheter device of claim 1, wherein each needle of the one or more needles on a respective fluid delivery element comprises a needle lumen that is in fluid communication with a corresponding port of the plurality of ports of the hub through a corresponding fluid delivery lumen of the respective fluid delivery element of the plurality of fluid delivery elements.

3. The catheter device of claim 1, wherein each needle of the one or more needles includes a taper at a distal end of the needle, the distal end of the needle being spaced away and extending in a direction facing away from the guidewire tube.

4. The catheter device of claim 1, wherein the guidewire tube further comprises a tip at a distal end of the guidewire tube, the tip comprises a proximal end having a proximal tip circumference and a tapered distal end, a distal end of the needle cover sheath configured to abut the tip when the plurality of fluid delivery elements are in the compressed and retracted position and disposed within the proximal tip circumference, and the distal end of the needle cover sheath configured to be spaced away from the tip when the plurality of fluid delivery elements are in the naturally biased and expanded position and disposed exterior to the proximal tip circumference.

5. The catheter device of claim 1, wherein the plurality of fluid delivery elements comprises at least two fluid delivery elements spaced apart on a shared plane.

6. The catheter device of claim 1, wherein the plurality of fluid delivery elements comprises at least four fluid delivery elements, each of the plurality of fluid delivery elements are equidistantly spaced apart from one another.

7. A catheter device comprising:

a hub including a plurality of ports, each port of the plurality of ports configured to receive a fluid;

a guidewire tube extending from the hub and defining a guidewire lumen comprising a longitudinal axis;

a plurality of fluid delivery elements extending from the hub and disposed about the guidewire tube, each fluid delivery element of the plurality of fluid delivery elements including a proximal portion, a distal portion, a hinge portion therebetween, and one or more needles on the distal portion extending in a direction perpendicular to the longitudinal axis of the guidewire lumen, a distal end of each fluid delivery element configured to adjust between (i) a naturally biased and expanded position at a spaced distance from the guidewire tube in which the proximal portion is angled with respect to the distal portion via the hinge portion and (ii) a compressed and retracted position abutting the guidewire tube in which the proximal portion is in alignment with the distal portion;

a compression sheath disposable over and slidably movable relative to the plurality of fluid delivery elements; and a needle cover sheath disposed over the compression sheath, the needle cover sheath movable relative to the compression sheath, the guidewire tube, and the plurality of fluid delivery elements extending to the hub through the compression sheath, wherein the plurality of fluid delivery elements are naturally biased in the naturally biased and expanded position when the compression sheath is proximally disposed in an expansion permitting position in which the compression sheath does not cover the hinge portion of each of the plurality of fluid delivery elements, and wherein the plurality of fluid delivery elements are in the compressed and retracted position when the compression sheath is distally disposed in a covering position in which the compression sheath covers the hinge portion of each of the plurality of fluid delivery elements, wherein each needle of the one or more needles on a respective fluid delivery element comprises a needle lumen that is in fluid communication with a corresponding port of the plurality of ports of the hub through a corresponding fluid delivery lumen of the respective fluid delivery element of the plurality of fluid delivery elements, and each needle of the one or more needles includes a taper at a distal end of the needle.

8. The catheter device of claim 7, wherein the distal end of the needle is spaced away and extending in a direction facing away from the guidewire lumen.

9. The catheter device of claim 7, wherein the guidewire tube further comprises a tip at a distal end of the guidewire tube, the tip comprises a proximal end having a proximal tip circumference and a tapered distal end, a distal end of the needle cover sheath configured to abut the tip when the plurality of fluid delivery elements are in the compressed and retracted position and disposed within the proximal tip circumference, and the distal end of the needle cover sheath configured to be spaced away from the tip when the plurality of fluid delivery elements are in the naturally biased and expanded position and disposed exterior to the proximal tip circumference.

10. The catheter device of claim 7, wherein the plurality of fluid delivery elements comprises at least two fluid delivery elements intersecting and spaced apart on a shared plane.

11. The catheter device of claim 7, wherein the plurality of fluid delivery elements comprises at least four fluid delivery elements, each of the plurality of fluid delivery elements are equidistantly spaced apart from one another.

12. A method of delivering a therapeutic fluid to a vessel, the method comprising:

positioning a catheter device within the vessel, the catheter device comprising:

a hub including a plurality of ports, each port of the plurality of ports configured to receive a fluid;

a guidewire tube extending from the hub and defining a guidewire lumen comprising a longitudinal axis;

a plurality of fluid delivery elements extending from the hub and disposed about the guidewire tube, each fluid delivery element of the plurality of fluid delivery elements including a proximal portion, a distal portion, a hinge portion therebetween, and one or more needles on the distal portion extending in a direction perpendicular to the longitudinal axis of the guidewire lumen, a distal end of each fluid delivery element configured to adjust between (i) a naturally biased and expanded position at a spaced distance from the guidewire tube in which the proximal portion is angled with respect to the distal portion via the hinge portion and (ii) a compressed and retracted position abutting the guidewire tube in which the proximal portion is in alignment with the distal portion;

a compression sheath disposable over and slidably movable relative to the plurality of fluid delivery elements;

a needle cover sheath disposed over the compression sheath, the needle cover sheath movable relative to the compression sheath, the guidewire tube, and the plurality of fluid delivery elements extending to the hub through the compression sheath; and moving the compression sheath of the catheter device proximally toward the hub to move from (i) a covering position in which the compression sheath covers the hinge portion of each of the plurality of fluid delivery elements such that the plurality of fluid delivery elements are in the compressed and retracted position to (ii) an expansion permitting position in which the compression sheath does not cover the hinge portion of each of the plurality of fluid delivery elements such that the plurality of fluid delivery elements are in the naturally biased and expanded position.

13. The method of claim 12, further comprising the one or more needles penetrating a vessel wall of the vessel when in the naturally biased and expanded position.

14. The method of claim 12, wherein each needle of the one or more needles on a respective fluid delivery element comprises a needle lumen that is in fluid communication with a corresponding port of the plurality of ports of the hub through a corresponding lumen of the respective fluid delivery element of the plurality of fluid delivery elements, and further comprising delivering the therapeutic fluid from the hub through the plurality of ports of the hub through a corresponding fluid delivery lumen of each of the plurality of fluid delivery elements and through a corresponding needle lumen of each needle of the one or more needles.

15. The method of claim 12, further comprising moving the compression sheath of the catheter device distally away from the hub to move from (i) the expansion permitting position in which the compression sheath does not cover the hinge portion of each of the plurality of fluid delivery elements such that the plurality of fluid delivery elements are in the naturally biased and expanded position to (ii) the covering position in which the compression sheath covers the hinge portion of each of the plurality of fluid delivery elements such that the plurality of fluid delivery elements are in the compressed and retracted position.

16. The method of claim 12, wherein each needle of the one or more needles includes a taper at a distal end of the needle, the distal end of the needle being spaced away and extending in a direction facing away from the guidewire tube.

17. The method of claim 12, wherein the plurality of fluid delivery elements comprises at least four fluid delivery elements, each of the plurality of fluid delivery elements are equidistantly spaced apart from one another.

18. The method of claim 12, wherein the guidewire tube further comprises a tip at a distal end of the guidewire tube, the tip comprises a proximal end having a proximal tip circumference and a tapered distal end, a distal end of the needle cover sheath configured to abut the tip when the plurality of fluid delivery elements are in the compressed and retracted position and disposed within the proximal tip circumference, and the distal end of the needle cover sheath configured to be spaced away from the tip when the plurality of fluid delivery elements are in the naturally biased and expanded position and disposed exterior to the proximal tip circumference.

* * * * *